United States Patent
Crutchfield et al.

(10) Patent No.: US 10,625,087 B2
(45) Date of Patent: Apr. 21, 2020

(54) THERAPY DELIVERY METHODS AND CIRCUITS FOR AN IMPLANTABLE MEDICAL DEVICE

(71) Applicant: Medtronic, Inc., Minneapolis, MN (US)

(72) Inventors: Randolph E. Crutchfield, Scottsdale, AZ (US); Lonny V. Cabelka, San Clemente, CA (US)

(73) Assignee: Medtronic, Inc., Minneapolis, MN (US)

( * ) Notice: Subject to any disclaimer, the term of this patent is extended or adjusted under 35 U.S.C. 154(b) by 920 days.

(21) Appl. No.: 14/260,313

(22) Filed: Apr. 24, 2014

(65) Prior Publication Data
US 2015/0306407 A1  Oct. 29, 2015

(51) Int. Cl.
| | |
|---|---|
| A61N 1/39 | (2006.01) |
| A61N 1/36 | (2006.01) |
| A61N 1/37 | (2006.01) |
| A61N 1/362 | (2006.01) |
| A61N 1/38 | (2006.01) |

(52) U.S. Cl.
CPC .......... *A61N 1/3925* (2013.01); *A61N 1/362* (2013.01); *A61N 1/36125* (2013.01); *A61N 1/3706* (2013.01); *A61N 1/385* (2013.01); *A61N 1/3906* (2013.01); *A61N 1/3912* (2013.01); *A61N 1/3956* (2013.01); *A61N 1/3975* (2013.01)

(58) Field of Classification Search
CPC .... A61N 1/3706; A61N 1/385; A61N 1/3925; A61N 1/3937
See application file for complete search history.

(56) References Cited

U.S. PATENT DOCUMENTS

| | | | |
|---|---|---|---|
| 4,949,720 A | 8/1990 | Thompson | |
| 5,201,865 A | 4/1993 | Kuehn | |
| 5,449,377 A * | 9/1995 | Adams | A61N 1/3956 607/7 |
| 5,470,341 A | 11/1995 | Kuehn et al. | |
| 5,527,346 A | 6/1996 | Kroll | |
| 5,755,742 A * | 5/1998 | Schuelke | A61N 1/3706 600/510 |
| 5,899,929 A * | 5/1999 | Thompson | A61N 1/3621 607/28 |
| 6,016,445 A | 1/2000 | Baura | |
| 6,107,699 A * | 8/2000 | Swanson | A61B 18/1492 307/112 |
| 6,175,765 B1 | 1/2001 | Sullivan et al. | |

(Continued)

OTHER PUBLICATIONS

(PCT/US2015/026974) PCT Notification of Transmittal of the International Search Report and the Written Opinion of the International Searching Authority, dated Jul. 20, 2015, 9 pages.

*Primary Examiner* — Michael J D Abreu (57) ABSTRACT

Techniques are disclosed for modulating the generation of charge current by operational circuitry included in an implantable medical device (IMD) for delivery of an induction stimulation pulse waveform by the IMD. The modulation may include modulating a charging circuit of the operational circuitry to facilitate the regulation of the induction stimulation pulse waveform. The techniques include monitoring an electrical parameter of a charging path during the delivery of the induction stimulation pulse and modulating the charging circuit based on the monitored electrical parameter.

16 Claims, 8 Drawing Sheets

(56) References Cited

U.S. PATENT DOCUMENTS

| | | |
|---|---|---|
| 6,317,628 B1 | 11/2001 | Linder et al. |
| 6,620,186 B2 | 9/2003 | Saphon et al. |
| 6,931,279 B2 | 8/2005 | Ousdigian et al. |
| 6,963,773 B2 | 11/2005 | Waltman et al. |
| 7,555,338 B2 | 6/2009 | Ostroff |
| 7,877,139 B2 | 1/2011 | Ostroff |
| 8,064,996 B2 | 11/2011 | Belk et al. |
| 8,340,762 B2 | 12/2012 | Vonk et al. |
| 8,423,136 B2 | 4/2013 | Ostoff |
| 8,452,399 B2 | 5/2013 | Wanasek |
| 2005/0154426 A1* | 7/2005 | Boveja ............... A61N 1/36007 607/45 |
| 2006/0241698 A1 | 10/2006 | Ostroff |
| 2007/0208394 A1* | 9/2007 | King ................ A61N 1/36071 607/62 |
| 2007/0270911 A1* | 11/2007 | Doerr .................. A61N 1/3621 607/5 |
| 2008/0091255 A1* | 4/2008 | Caparso ............ A61N 1/36114 607/116 |
| 2010/0324618 A1 | 12/2010 | Wanasek |
| 2011/0077698 A1* | 3/2011 | Tsampazis ............... A61N 1/08 607/2 |
| 2012/0116483 A1 | 5/2012 | Yonezawa et al. |
| 2012/0143286 A1* | 6/2012 | Hahn ................ A61N 1/36132 607/59 |
| 2012/0197325 A1 | 8/2012 | Sauer et al. |
| 2013/0035735 A1 | 2/2013 | Kroll |
| 2013/0241628 A1 | 9/2013 | Zhang |

\* cited by examiner

THERAPY DELIVERY METHODS AND CIRCUITS FOR AN IMPLANTABLE MEDICAL DEVICE

FIELD

The present invention relates generally to implantable medical devices. In particular, the disclosure relates to methods, components, and circuits for therapy delivery by the implantable medical devices.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with an implantable medical device (IMD). For example, an implanted IMD may detect an arrhythmia, such as ventricular fibrillation, and deliver one or more electrical pulses to stop the arrhythmia and allow the heart to reestablish a normal sinus rhythm.

Examples of such IMDs include subcutaneous implantable cardioverter/defibrillator (SICD) systems that provide synchronous cardioversion shocks and/or asynchronous defibrillation shocks and subcutaneous pacemaker/cardioverter/defibrillator (SPCD) systems that provide additional staged therapies of anti-tachyarrhythmia pacing, synchronous cardioversion shocks and asynchronous defibrillation shocks. In general, the IMDs deliver a first pulse at a first energy level upon detecting an arrhythmia and, if the arrhythmia is not stopped, deliver additional pulses at increasing energy levels until the arrhythmia is stopped or the programmed progression of pulses has been exhausted.

Typically, threshold testing is performed to evaluate the effectiveness of an IMD in ending episodes of arrhythmia. For example, the energy levels or waveforms of pulses delivered by the IMD, the sensitivity of the IMD to detect ventricular fibrillation, or the position of the electrodes used to deliver the pulses, can be configured as necessary to assure the effectiveness of the IMD. The threshold testing may be performed during the implantation process, during subsequent follow-up sessions and/or during the automatic configuration sessions initiated by the IMD. One method of testing an IMD's capability to reliably defibrillate the heart involves induction of an episode of an arrhythmia in the patient's heart, and then allowing the IMD to detect and terminate the induced arrhythmia. The IMD itself has the capability of inducing arrhythmia during the threshold testing procedures.

The IMD induces an arrhythmia by delivering a pulse during the period of vulnerability within a cardiac cycle, e.g., during or near the T-wave, delivering a high frequency pulse train, delivering direct current, or other known methods for inducing the fibrillation. The clinician may program the stimulation parameters for the induction attempt, such as the timing, amplitude, or other characteristics of a T-wave shock. If the induction attempt fails, the new stimulation parameters are used for another induction attempt.

When an induction attempt succeeds, the IMD can fail to detect the arrhythmia, or fail to stop the arrhythmia. In such cases, the detection algorithm or the pulse progression must be modified. The process repeats until successful arrhythmia induction, detection, and defibrillation occur such that the effectiveness of the IMD is confirmed.

The process of confirming the effectiveness of an IMD can be time and resource consuming both for the clinician and for the IMD. For example, a clinician programs the IMD to execute an initial arrhythmia detection algorithm, and programs an initial progression of pulses to be delivered in response to a detected arrhythmia. The clinician then programs the IMD to induce the heart to fibrillate, so that the programmed detection algorithm and pulse progression can be tested. During automatic configuration sessions, the device may also consume a large amount of the internally stored energy to perform those functions. Accordingly, there remains a need for improved circuits and methods for therapy delivery.

SUMMARY

It is desired to perform threshold testing to evaluate the efficacy of the therapy delivered by a subcutaneous or substernal implantable medical device (SIMD). The threshold testing may be performed during the implant procedure, or during an IMD checkup procedure, or during automatic configurations of the IMD over the lifetime of the device.

The techniques described herein facilitate the modulation of a charging circuit of SIMD in the generation of charge current for delivery of a stimulation pulse waveform. Aspects of the disclosure include monitoring an electrical parameter of a charging path during the delivery of the stimulation pulse waveform and modulating the charging circuit based on the monitored electrical parameter. In some embodiments, a modulation device may be coupled to the charging circuit to regulate the generation of energy by the charging circuit.

In some aspects, the SIMD includes a monitoring device that is configured to measure an electrical parameter of a charging path. In some embodiments, the monitoring devices measure the current flowing through the charging path. The monitoring devices are configured to measure the charge current flowing through the charging path. In alternative embodiments, the monitoring devices are configured to measure the voltage generated across a load on the charging path.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

In conventional implantable medical systems, the generation of stimulation pulse waveforms may be performed by charging capacitors that are coupled to the output circuit for storage of a pre-defined capacity of energy, with the capacity of the stored energy being based upon the requirements for the energy that is to be delivered in accordance with a pre-programed treatment regimen. For example, such capacitors are charged up to a pre-defined capacity to store an amount of energy that is utilized for delivery of stimulation pulse waveforms in accordance with a selected treatment regimen.

In accordance with embodiments of the present disclosure, the current for generating a stimulation pulse may be regulated in real time during delivery of the stimulation pulse waveform while also accounting for energy losses during delivery of the stimulation pulse. Such a stimulation pulse waveform may be configured as an induction stimulation pulse waveform that induces an arrhythmia in a patient. The techniques of the present invention that enable real-time regulation of the charge current for a stimulation pulse waveform also facilitate a reduction in the electrical component count of the output circuit. Moreover, the current regulation reduces the thermal stress on the components of the charging circuit, energy storage capacitors, and the output circuit.

Currently, implantable medical devices (IMD), such as the implantable cardioverter/defibrillator (ICD), use endocardial or epicardial leads which extend from the ICD housing through the venous system to the heart. Electrodes positioned by the leads in or adjacent to the heart are used for therapy delivery and sensing functions. Cardioversion and defibrillation shocks are generally applied between a coil electrode carried by one of the leads and the ICD housing, which acts as an active can electrode. A subcutaneous or substernal implantable medical device (SIMD) differs from the more commonly used IMD in that the housing and leads are typically implanted subcutaneously such that the sensing and therapy are accomplished subcutaneously. The SIMD does not require leads to be placed in or on the cardiac tissue. Instead, the SIMD makes use of one or more electrodes on the housing, together with one or more leads that carry one or more electrodes for therapy delivery and/or sensing, which are implanted in the subcutaneous or substernal space.

The disclosure describes techniques, components, devices, and methods for performing threshold testing of an SIMD. In this disclosure, the stimulation pulses that are delivered for the threshold testing will be referred to as arrhythmia induction stimulation pulses (or simply as induction stimulation pulses).

In this disclosure, "substernal space" refers to the region defined by the undersurface between the sternum and the body cavity but not including the pericardium. In other words, the region is dorsal to the sternum and ventral to the ascending aorta. The substernal space may alternatively be referred to by the terms "retrosternal space" or "mediastinum" or "infrasternal" as is known to those skilled in the art and includes the region referred to as the anterior mediastinum. For ease of description, the term substernal space will be used in this disclosure, it being understood that the term is interchangeable with any of the other aforementioned terms.

In this disclosure, the term "extra-pericardial" space refers to the region around, but not in contact with, the outer heart surface. The region defined as the extra-pericardial space includes the gap, tissue, bone, or other anatomical features around the perimeter of, and adjacent to, but not in contact with the pericardium.

In this disclosure therapy stimulus pulse information such as stimulus amplitude, duration, rate, and/or waveform type (e.g., mono-phasic, bi-phasic, tri-phasic, or multi-phasic, etc.) and the like are included under the rubric of "stimulation parameters."

Figure 1:
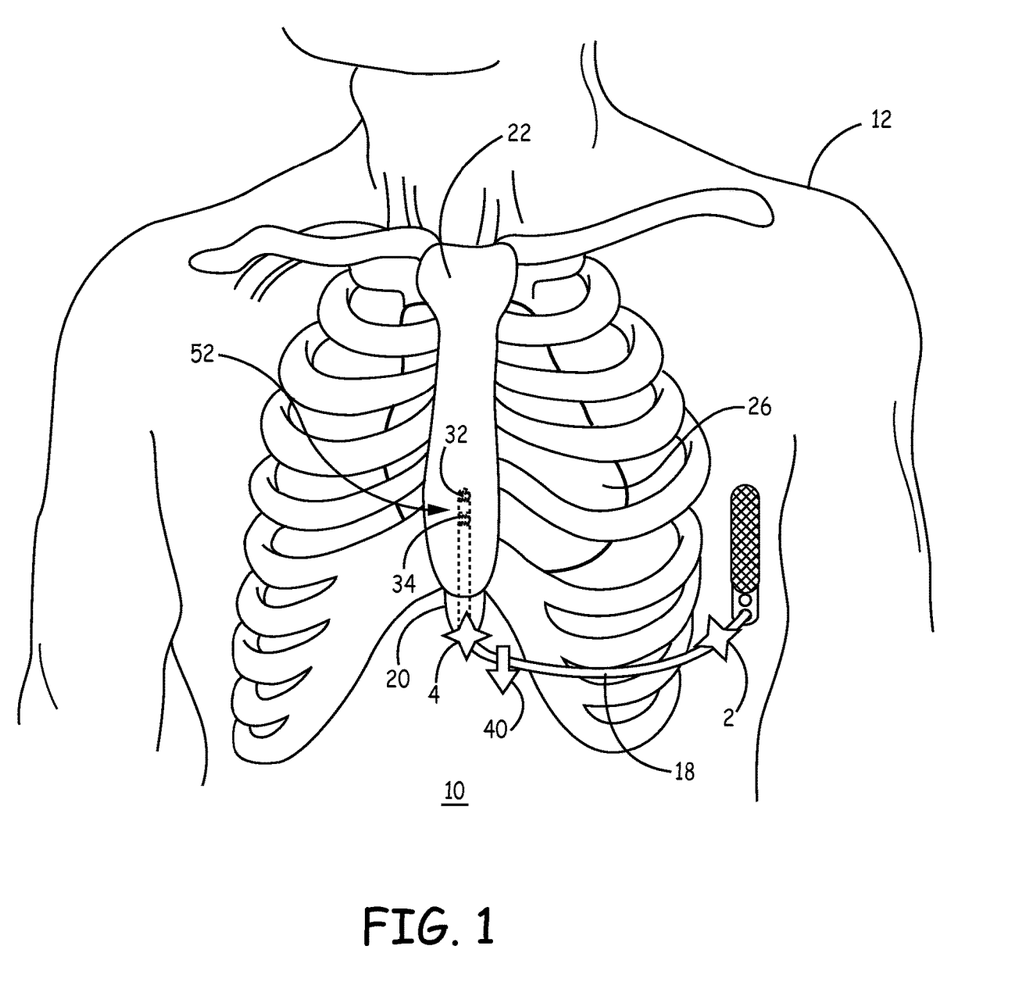
FIG. 1 is a front view of a patient implanted with an implantable cardiac system.
Figure 2:
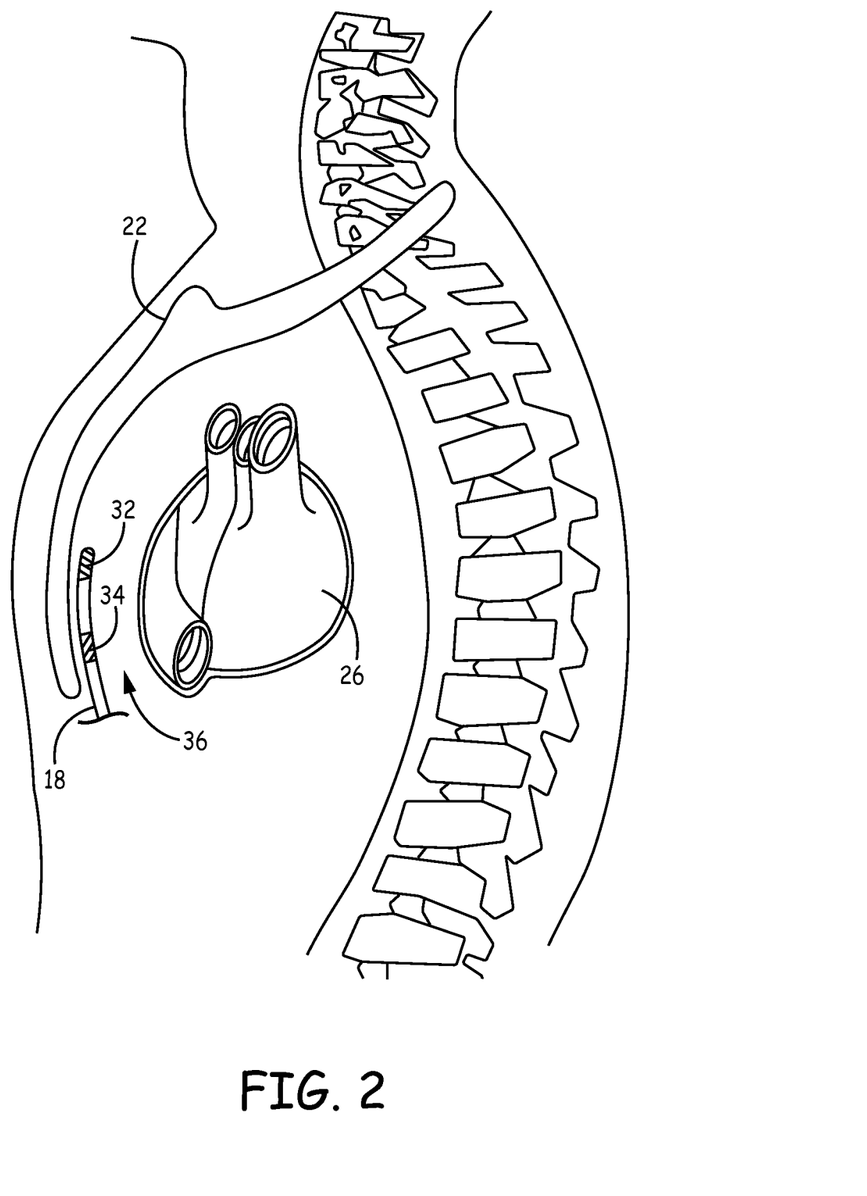
FIG. 2 is a side view of the patient implanted with the implantable cardiac system.

FIGS. 1-2 are conceptual diagrams of a patient 12 implanted with an exemplary implantable cardiac system 10. FIG. 1 is a front view of patient 12 implanted with implantable cardiac system 10. FIG. 2 is a side view patient 12 with implantable cardiac system 10.

Implantable cardiac system 10 includes a subcutaneous/substernal implantable medical device (SIMD) 14 connected to a lead 18. The lead 18 may be utilized for sensing and/or to provide an electrical stimulation pulse such as pacing or defibrillation. Lead 18 includes electrodes 32 and 34 that may be configured for delivery of the stimulation pulse. In addition, or alternatively, the electrodes 32, 34 may be configured for sensing.

SIMD 14 may provide stimulation pulse therapy and/or sense electrical activity of heart 26 via a combination of delivery/sensing vectors that include combinations of electrodes 32 and 34 and the housing or can electrode of SIMD 14. For example, SIMD 14 may deliver therapy or obtain electrical signals sensed using a delivery/sensing vector between electrodes 32 and 34, or using a delivery/sensing vector between electrode 32 and the conductive housing or can electrode of SIMD 14, or using a delivery/sensing vector between electrode 34 and the conductive housing or can electrode of SIMD 14, or a combination thereof. In this manner, sensing and stimulation pulses including defibrillation therapy, ATP therapy or post shock pacing (or other pacing therapy) may be provided in an ICD system without entering the vasculature or the pericardial space, nor making intimate contact with the heart.

The electrodes 32 and 34 may be located near a distal end of lead 18. Electrodes 32 and 34 may comprise ring electrodes, hemispherical electrodes, coil electrodes, helix electrodes, or other types of electrodes, or combination thereof. Electrodes 32 and 34 may be the same type of electrodes or different types of electrodes.

The lead body of lead 18 also includes one or more elongated electrical conductors (not illustrated) that extend through the lead body from the connector assembly of SIMD 14 provided at a proximal lead end to electrodes 32, 34. The lead body of lead 18 may be formed from a non-conductive material, including silicone, polyurethane, fluoropolymers, mixtures thereof, and other appropriate materials, and shaped to form one or more lumens within which the one or more conductors extend. However, the techniques are not limited to such constructions.

The one or more elongated electrical conductors contained within the lead bodies of leads 16 and 18 may engage with respective ones of electrodes 32, 34. The respective conductors may electrically couple to circuitry, such as a therapy module or a sensing module, of SIMD 14 via connections in connector assembly, including associated feedthroughs. The electrical conductors transmit therapy from a therapy module within SIMD 14 to one or more of electrodes 32, 34 and transmit sensed electrical signals from one or more of electrodes 32, 34 to the sensing module within SIMD 14.

In the example illustrated in FIGS. 1-2, SIMD 14 is implanted subcutaneously on the left midaxillary of patient 12. SIMD 14 may, however, be implanted at other subcutaneous locations on patient 12. The lead 18 may be inserted through an incision 2 or 4 on the patient's body for subcutaneous and/or extrapericardial implantation as will be described in more detail below.

Lead 18 includes a proximal end that is connected to SIMD 14 and a distal end that includes one or more electrodes. Lead 18 may be implanted within the mediastinum such that one or more electrodes 32 and 34 are located over a cardiac silhouette of the ventricle as observed via fluoroscopy. In the example illustrated in FIGS. 1-2, lead 18 is located substantially centered under sternum 22. Lead 18 extends subcutaneously from SIMD 14 toward xiphoid process 20. At a location near xiphoid process 20 lead 18 bends or turns and extends superior upward in the substernal space. In one example, lead 18 may be placed in the mediastinum 36 and, more particularly, in the anterior mediastinum. The anterior mediastinum is bounded laterally by pleurae, posteriorly by pericardium, and anteriorly by sternum 22. In other instances, however, lead 18 may be implanted such that it is offset laterally from the center of sternum 22. Alternatively, lead 18 may be placed such that a therapy vector between one of electrodes 32, 34 and a housing or can electrode of SIMD 14 is substantially across the ventricle of heart 26. Although described herein as being implanted in the substernal space, the mediastinum, or the anterior mediastinum, lead 18 may be implanted in other extra-pericardial locations.

The configuration described above in FIGS. 1-2 is directed to providing ventricular pacing via lead 18. In situations in which atrial pacing is desired in addition to or instead of ventricular pacing, lead 18 may be positioned further superior. A pacing lead configured to deliver pacing pulses to both the atrium and ventricle may have more electrodes. For example, the pacing lead may have one or more electrodes located over a cardiac silhouette of the atrium as observed via fluoroscopy and one or more electrodes located over a cardiac silhouette of the ventricle as observed via fluoroscopy. In some instances, two substernal pacing leads may be utilized with one being an atrial pacing lead implanted such that the electrodes are located over a cardiac silhouette of the atrium as observed via fluoroscopy and the other being a ventricle pacing lead being implanted such that the electrodes are located over a cardiac silhouette of the ventricle as observed via fluoroscopy.

SIMD 14 may include a housing that forms a hermetic seal that protects components of SIMD 14. The housing of SIMD 14 may be formed of a conductive material, such as titanium. SIMD 14 may also include a connector assembly (also referred to as a connector block or header) that includes electrical feedthroughs through which electrical connections are made between conductors within lead 18 and electronic components included within the housing. Housing may enclose one or more processors, memories, transmitters, receivers, sensors, sensing circuitry, therapy circuitry and other appropriate components as is known in the art. SIMD 14 is configured to be implanted in a patient, such as patient 12.

As shown in FIG. 1, an anchoring mechanism 40 may be provided along the lead body to couple the lead 18 at an access point 4 through which the distal end of the lead 18 is inserted into the substernal space. The access point 4 is any location that provides access into the substernal space. In one exemplary embodiment, the access point 4 is adjacent to or below the xiphoid process (also referred to as "subxiphoid"). The access point may also be at the notch (not shown) that connects the xiphoid process to the sternum. In other embodiments, the substernal space may also be accessed through the manubrium. The anchoring mechanism 40 is fixedly-coupled to cartilage, musculature, tissue or bone at the entry point into the substernal space at or near the access point at which site the body of the lead 18 transitions from the subcutaneous tissue into the substernal space of patient 12.

The examples illustrated in FIGS. 1-2 are exemplary in nature and should not be considered limiting of the techniques described in this disclosure. In other examples, SIMD 14 and lead 18 may be implanted at other locations. For example, SIMD 14 may be implanted in a subcutaneous pocket in the right chest. In this example, lead 18 may be extend subcutaneously from the device toward the manubrium of the sternum and bend or turn and extend subcutaneously inferiorily from the manubrium of the sternum, substantially parallel with the sternum.

In addition, it should be noted that system 10 may not be limited to treatment of a human patient. In alternative examples, system 10 may be implemented in non-human patients, e.g., primates, canines, equines, pigs, and felines. These other animals may undergo clinical or research therapies that may benefit from the subject matter of this disclosure.

Figure 3:
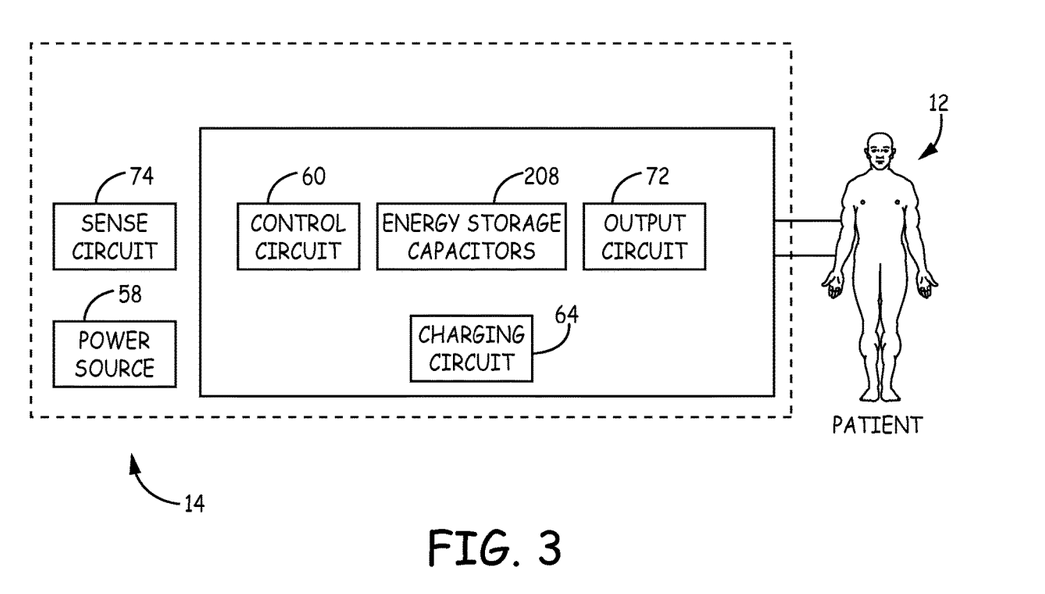
FIG. 3 is a block diagram of a subcutaneous/substernal SIMD of the implantable cardiac system.

FIG. 3 is a block diagram of SIMD 14 that is connected to a patient 12. The SIMD 14 is shown having operational circuitry that includes a control circuit 60 that is connected to energy storage capacitors 208a, and 62b (collectively "62") via a charging circuit 64. During the operation of the SIMD 14, the control circuit 60 controls various functions of the SIMD 14 such as stimulation pulse delivery or sensing. For example, the control circuit 60 controls the delivery of stimulation pulses for threshold testing to maximize the efficiency of the therapy delivered based on a selected one or more therapy programs, which may be stored in memory. Among other things, the control circuit 60 issues signals to regulate the charging circuit 64 to charge the capacitors 208 to a desired voltage level. Feedback on the voltage level of the capacitors 208 is provided to the control circuit 60. A power source 58 is provided in SIMD 14 and may be coupled to charging circuit 64 to provide the energy that is utilized to generate the stimulation pulses.

The control circuit 60 may include any type of circuitry that can issue control signals for controlling the various functions of SIMD 14. For example, the control circuit 60 is generally representative of a processor and associated memory. The memory, for example, may include computer readable instructions that, when executed by processor, cause the components of the SIMD 14 to perform various functions attributed to them. For example, the memory may include any non-transitory, computer-readable storage media including any combination of one or more of a volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

To facilitate therapy delivery, the SIMD 14 may deliver the therapy in response to sensed physiological conditions. As such, SIMD 14 may include sense circuitry 74 that is coupled to the control circuit 60. For example, sense circuitry 74 may include one or more sense amplifier circuits receiving cardiac signals to monitor the heart (e.g., sense evoked responses of the heart), such as described, for example, in U.S. Pat. No. 5,861,013, to Peck et al., or, for example, in U.S. Pat. No. 5,117,824, to Keimel et al., entitled Apparatus for Monitoring Electrical Physiologic Signals," both of which are incorporated herein by reference in their entirety.

The functions attributed to SIMD 14 herein may be embodied as one or more processors, hardware, firmware, software, or any combination thereof. Depiction of different features as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components. For example, sensing circuitry 74 for receiving and converting analog electrical signals received from other SIMD modules or sensors may be implemented in hardware and software included in control circuit 60.

After charging to a desired level, the energy stored in the capacitors 208 may be delivered to the patient 12 in the form of stimulation pulses. Control circuit 60 may be connected to the output circuit 72 to control the delivery of the stimulation pulses. The application of appropriate control signals causes the output circuit 72 to deliver the energy received from the capacitors 208 in the form of stimulation pulses. The energy is delivered to the patient 12 attached to the SIMD 14 over a set of electrodes that may be selected from one or more of the electrodes on the lead(s) (e.g., 32, 34), and/or the can/housing electrode. The control circuit 60 may verify the integrity of the output circuit 72 before and during the transfer of the stimulation pulse. In accordance with aspects of the present application, some of the components of SIMD 14 are disclosed in FIGS. 4-6.

To avoid unnecessarily obscuring the inventive aspects of the disclosure, it should be understood that numerous other components of SIMD 14 have not been shown. Examples of such additional components and/or circuit configurations for the operational circuitry employed in SIMD 14 can take any of the known forms that detect a tachyarrhythmia from the sensed ECG and provide cardioversion/defibrillation shocks as well as post-shock pacing as needed while the heart recovers. Such components include circuitry for powering and controlling various sensing and therapy delivery functions. An exemplary simplified block diagram of such circuitry adapted to function employing the sensing and therapy delivery electrodes described herein is set forth in U.S. Pat. No. 7,647,095, "Method and Apparatus for Verifying a Determined Cardiac Event in a Medical Device Based on Detected Variation in Hemodynamic Status" to Bhunia and in U.S. Pat. No. 8,155,740, "Constant Current Pacing Apparatus and Pacing Method" to Wanasek, which are both incorporated herein by reference in their entirety. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the SIMD 14 and an external programmer.

Figure 4:
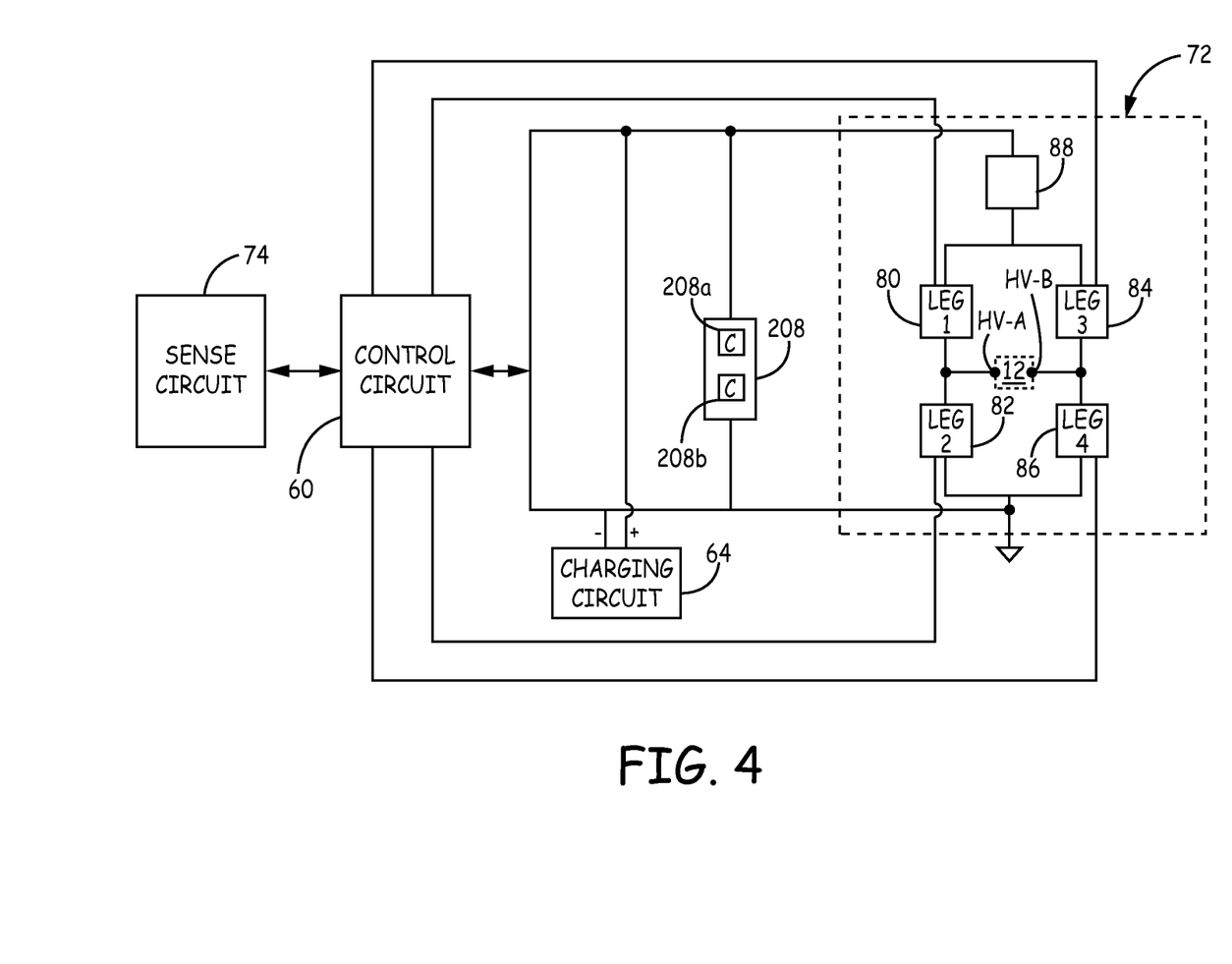
FIG. 4 illustrates an exemplary schematic showing a portion of the operational circuitry of the SIMD in accordance with an embodiment of the disclosure.

FIG. 4 illustrates an exemplary schematic showing a portion of the operational circuitry of SIMD 14 in accordance with an embodiment of the disclosure. The output circuit 72 allows the controlled delivery of energy from the capacitors 208 to the patient 12. The energy may be delivered to provide one or more functions of the SIMD 14 such as therapy delivery, or threshold testing for pacing or defibrillation therapies. Collectively, the energy delivered for various therapies (such as pacing, defibrillation) and threshold testing is performed in accordance with a treatment regimen that may be pre-programed into SIMD 14 (such as the aforementioned processor and/or memory) and updated during the operational life of the SIMD 14.

The output circuit 72 includes four switches 80, 82, 84, and 86 that are interconnected. As is shown in FIG. 4, the switches 80, 82, 84, and 86 are arrayed to define a configuration that is commonly referred to as a "H-bridge". In other words, the four interconnected switches are arrayed having switches 80 and 84 that are connected to the high side and switches 82 and 86 that are connected to the low side.

As shown in FIG. 4, the intersection of the switches 80-86 includes HV-A and HV-B terminals that couple the output circuit 72 to the therapy delivery and sense electrodes. The SIMD 14 delivers stimulation pulses to patient 12 typically through at least two electrodes (e.g., via one or more of electrodes 32, 34 (FIGS. 1, 2), and/or the can electrode) that are coupled to terminal HV-A and terminal HV-B according to predetermined therapy or other treatment regimens.

Switches 80 and 84 are coupled through a discharge switch 88 to a positive terminal of the capacitors 208. Discharge switch 88 is controlled by control circuit 60 to be biased in a conducting (closed) state and remain in the conducting state during discharge of the capacitors 208. Switches 82 and 86 are coupled to a negative terminal of the capacitors 208. The selection of one or more of the switches 80, 82, 84, and 86 under control of control circuit 60 may be used to provide one or more functions. For example, selection of certain switches in one or more configurations may be used to provide one or more types of stimulation pulses such as pacing, cardioversion, or defibrillation, or may be used for threshold testing, or may be used to remove DC polarization of the tissue-to-electrode interface, etc.

In accordance with aspects of this disclosure, the switches 80, 82, 84, 86 are biased into one of a conducting or non-conducting state to deliver one or more stimulation pulses to effect various predetermined operations of the SIMD 14. The switches 80-86 may be implemented as power semiconductor devices that may be operated as an electronic switch. Examples of power semiconductor devices include thyristors, silicon controlled rectifiers (SCRs), insulated-gate bipolar transistors (IGBTs), metal oxide semiconductor field effect transistors (MOSFETs such as N-channel or P-Channel MOSFETs, BiMOSFETs), either employed alone or in electrical series with high voltage thyristors or "triacs" or having a current blocking component such as a diode connected across the source and drain, a body diode, etc, associated therewith. The discharge switch 88 may be implemented as a power semiconductor device operated as an electronic switch (including for example an IGBT, or a BiMOSFET, or any of the other devices disclosed herein). As is known in the art, such semiconductor devices may be switched into conduction based on signals that are issued by control circuit 60 alone, or by dedicated drive circuits which respond to low voltage control signals, or a combination of both.

Control circuit 60 issues control signals that cause the output circuit 72 to be configured in one of a plurality of configurations each of which is selected to provide one or more functions of the SIMD 14. For example, in accordance with an embodiment, the SIMD 14 provides a biphasic therapy stimulation pulse to the patient in the following manner. Charge energy is delivered to capacitors 208 and the switches 80, 86, and 88 are biased in a conducting state in order to provide a path from the capacitors 208 to electrodes (e.g., 32, 34) for the application of a first phase of a stimulation pulse to the patient 12. The energy discharged from the capacitors is conducted from the positive terminal of the capacitors 208, through switch 80, across the patient 12, back through switch 86 to the negative terminal of the capacitors 208. The first phase of the biphasic pulse therefore applies a positive pulse across the electrodes coupled to terminals HV-A and HV-B.

Before the capacitors 208 are completely discharged, switches 80 and 86 are biased in a non-conducting state in preparation for application of the second phase of the biphasic pulse. For example, biasing the switches 80-86 in a non-conducting state may be achieved by opening switch 88 to shut off the current flow in accordance with one embodiment. In other embodiments, the control circuit 60 may issue signals to control the biasing of each of the switches 80-88.

After the end of the first phase of the biphasic therapy stimulation pulse, the switches 88, 84 and 82 are biased in a conducting state to start the second phase of the biphasic pulse. Switches 84 and 82 provide a path to apply a negative stimulation pulse to the patient 12. With reference to FIG. 4, the energy is conducted from the positive terminal of the capacitors 208, through switch 84, across the electrodes that are coupled to the patient 12, and out through switch 82 to the negative terminal of the capacitors 208. The polarity of the second phase of the therapy stimulation pulse is therefore opposite in polarity to the first phase of the pulse.

In another example, the SIMD 14 will perform threshold testing to determine optimum stimulation parameters for therapy delivery. SIMD 14 induces fibrillation of heart 12, e.g., ventricular fibrillation, to test the effectiveness of the SIMD 14 in detecting and stopping the fibrillation. SIMD 14 induces fibrillation according to a fibrillation induction protocol included in the patient's treatment regimen, and is capable of employing a plurality of fibrillation protocols to induce fibrillation. Exemplary fibrillation induction protocols include delivery of an electrical pulse to heart 12 during the T-wave of a cardiac cycle, delivery of a high-frequency pulse train, and delivery of direct current. The disclosure is not limited to the exemplary induction protocols, and SIMD 14 can induce fibrillation according to any of a number of fibrillation induction protocols known in the art. SIMD 14 detects fibrillation employing one or more fibrillation detection techniques known in the art. SIMD 14 can be programmed to deliver a progression of therapies, e.g., pulses with increasing energy levels, until the detected fibrillation of heart 12 is stopped.

Accordingly, techniques of the present invention utilize the output circuit 72 in a predetermined arrangement to deliver the stimulation pulse(s) for the therapy delivery in accordance with the patient's treatment regimen. As will be discussed in more detail below, charge current is controlled during generation and delivery of a stimulation pulse waveform. For ease of description, the generated stimulation pulse waveforms of the disclosure will be described in the context of induction stimulation pulse waveforms for threshold testing, it being understood that the techniques for generating stimulation pulses can be applied to any other forms of therapy that are included in a patient's treatment regimen.

Figure 5:
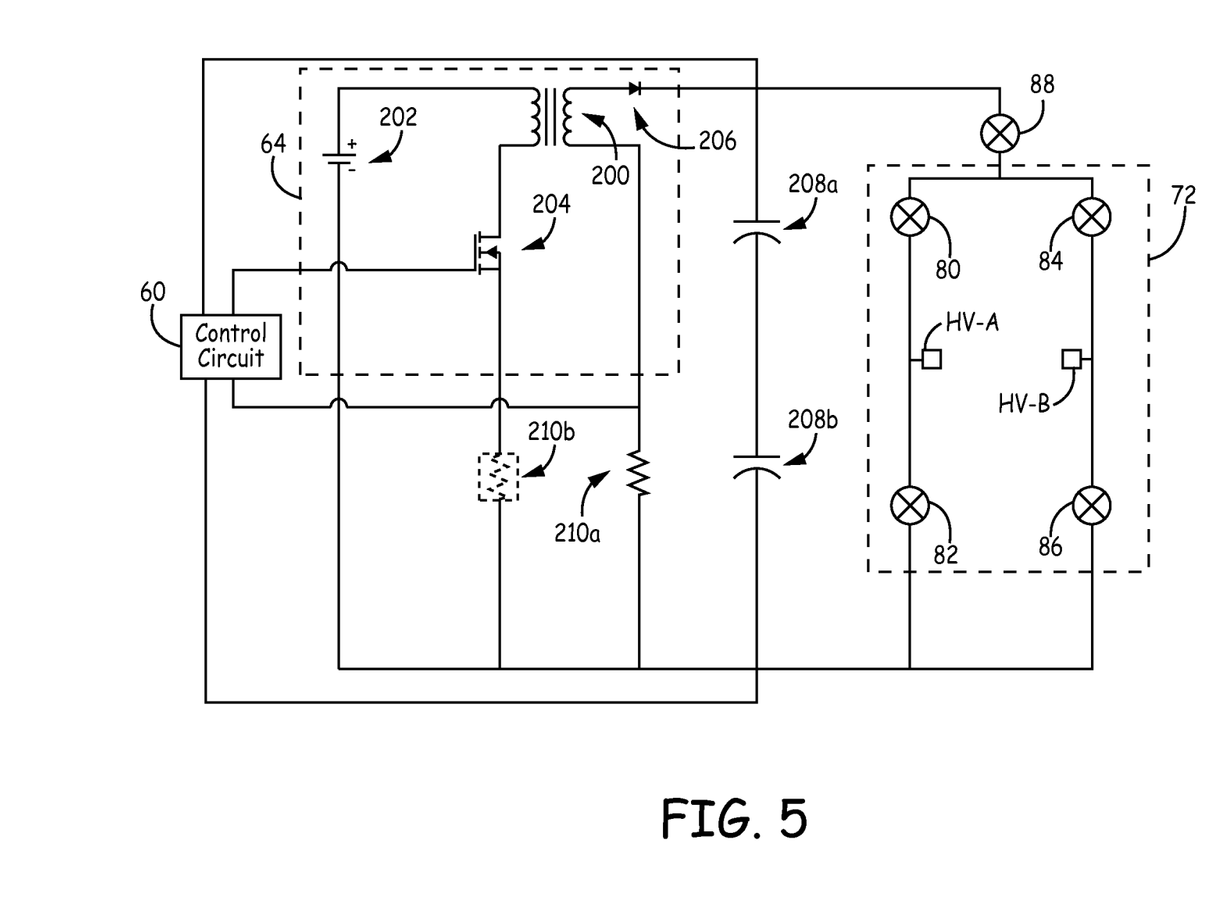
FIG. 5 shows an exemplary schematic diagram of a portion of the operational circuitry of the SIMD of FIG. 4 in accordance with embodiments of the disclosure.
Figure 6:
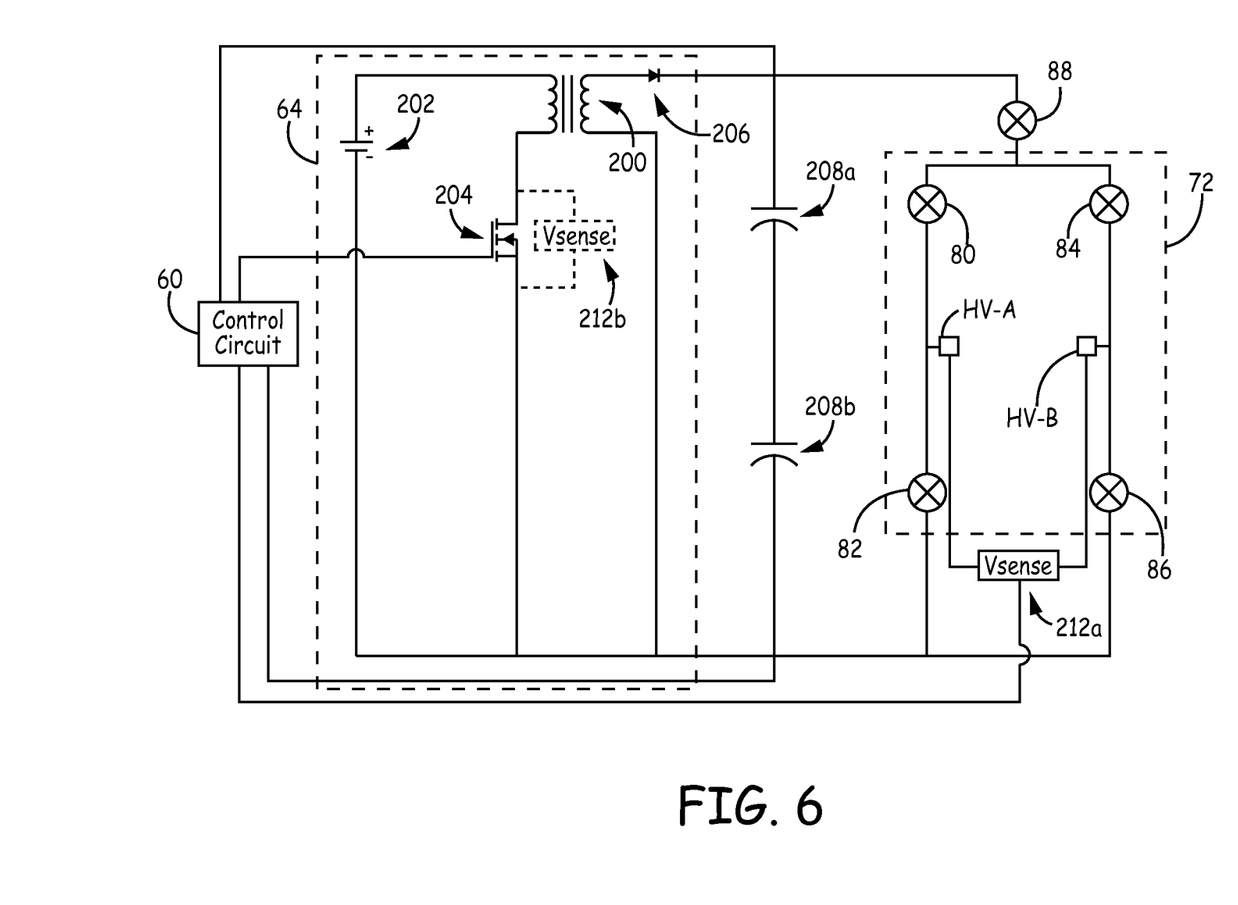
FIG. 6 shows an exemplary schematic diagram of a portion of the operational circuitry of the SIMD of FIG. 4 in accordance with alternative embodiments of the disclosure.

Exemplary embodiments of the charging circuit 72 of FIG. 4 are shown in FIGS. 5 and 6. As described in reference to FIG. 4, the four output switches 80, 82, 84, and 86 allow the transfer of energy from the capacitors 208. Switches 80-84 may be implemented as any of the power semiconductor devices mentioned above. In such an embodiment, the semiconductor devices may be controlled by the control circuit 60 from a conducting to a non-conducting state. The four output switches 80, 82, 84, and 86 can be switched from a non-conducting to a conducting condition based on control signals provided by the control circuit 60.

FIGS. 5 and 6 show exemplary schematic diagrams of a portion of the operational circuitry of SIMD 14, such as that illustrated in FIG. 4, in accordance with embodiments of the disclosure. The diagram depicts some of the components of the charging circuit 64 of FIG. 4 in detail. Charging circuit 64 includes a voltage converter 200, a power input 202, and a switch 204.

The voltage converter 200 may be implemented in one embodiment to include a rectifier diode 206 that is coupled to a flyback transformer, such as that described in U.S. Pat. No. 7,167,074 to Fenner et al., which is incorporated herein by reference. In other embodiments, a voltage converter may include one (or more) primary side(s) that is coupled to one (or more) secondary side(s). For example, the voltage converter may include one primary side that is coupled to as many as six secondary sides. The primary side of the converter 200 is coupled to the power input 202 to electrically couple the converter 200 to an energy source such as the battery 58 (FIG. 3). The output of the converter 200 is taken from the secondary side for the delivery of energy to the output circuit 72.

In the illustrative embodiment, the rectifier diode 206 is coupled in series with the secondary side of the flyback transformer as shown in FIGS. 5 and 6. Rectifier diode 206 defines the direction of current flow from each secondary side of the transformer of the converter 200 to the output circuit 72 along a delivery path, while blocking the reverse flow of current back to the secondary side of the transformer. In some embodiments, one or more capacitors 208a, 208b (collectively, "208") may be coupled between the rectifier diode 206 and the output circuit 72.

Switch 204 couples the power input 202 to the voltage converter 200. Power input 202 may designate the input nodes that couple to a power source, such as power source 58, or to a separate energy source that is provided for powering charging circuit 64. The switch 204 may be implemented as any of the power semiconductor devices discussed above with reference to FIG. 4. For ease of discussion, the illustrative switch 204 will be described as a FET. Control circuit 60 issues a modulation control signal that is configured to modulate the charging circuit 64 during generation of charge current for the stimulation pulse. The modulation of charging circuit 64 may be achieved based on the relative timing of the actuation of switch 204 in a conducting state and a non-conducting state.

When switch 204 is implemented as a FET, the gate is coupled to control circuit 60 so that modulation signals issued by the control circuit 60 will actuate the switch 204 to be biased in the conducting state or the non-conducting state to close and open the switch 204, respectively. The modulation signals control the frequency at which the switch 204 is biased in the conducting states and non-conducting states as well as the duration of each of the states. Each successive pair of conducting and non-conducting states defines a charge cycle.

The voltage converter 200 will generate charge current that is regulated as a function of the actuation of switch 204. In other words, the frequency and duration of the closing and opening of switch 204 modulates the energy that is generated by the voltage converter 200 to charge up the capacitors 208 for delivery of a stimulation pulse. Without intending to be bound by theory, closing the switch 204 will allow magnetic energy to build up in the primary windings of the voltage converter 200. In response to opening the switch 204, the energy (voltage across output terminals) at the secondary of voltage converter 200 (or multiple secondary sides in some implementations) will flow from voltage converter 200 to charge up the capacitors 208.

Figure 7A:
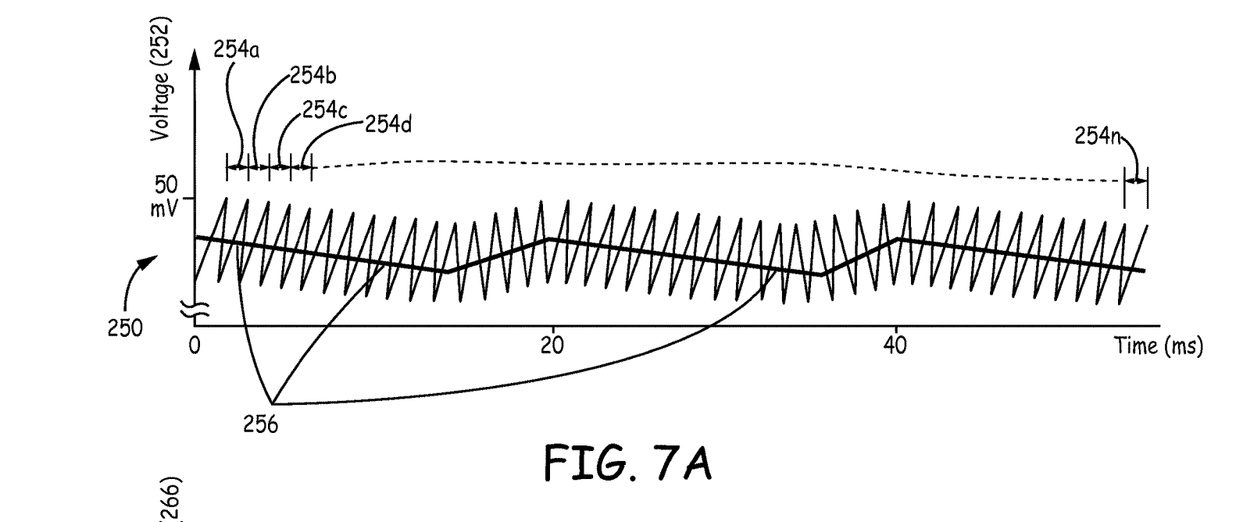
FIG. 7A depicts an exemplary graph of a voltage waveform generated in accordance with embodiments of the disclosure.
Figure 7B:
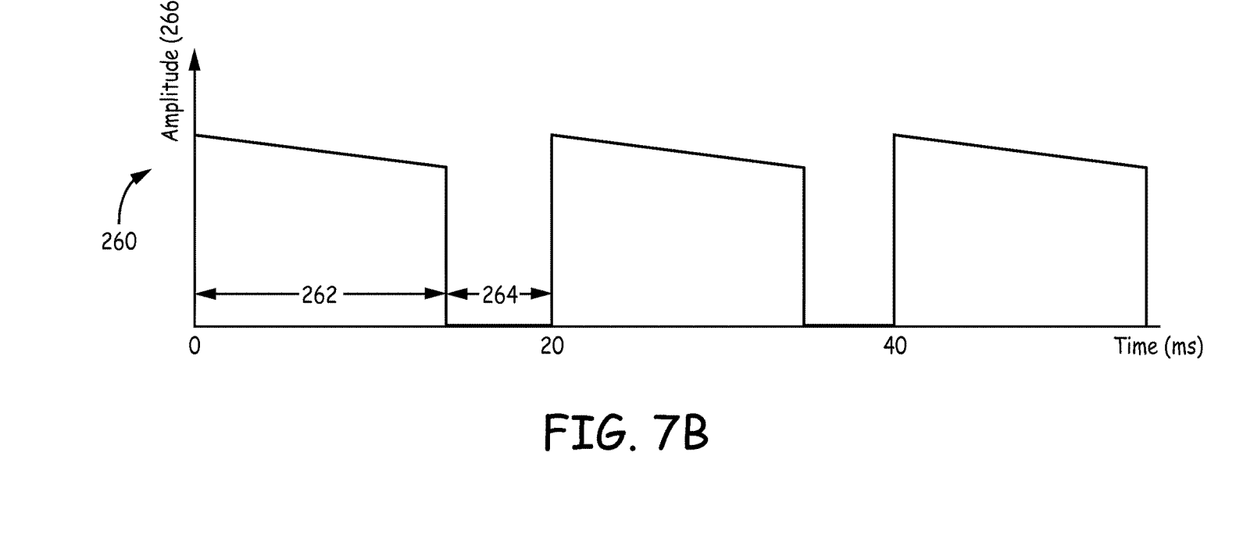
FIG. 7B depicts an exemplary graph of a stimulation pulse waveform delivered in accordance with embodiments of the disclosure.

As such, for any given charge cycle, the voltage converter 200 will generate charge during a conducting state of switch 204 and discharge the charge during the immediately subsequent non-conducting state of switch 204 to generate charge current for the stimulation pulse. As shown in more detail in FIG. 7, a stimulation pulse waveform is generated by the charge current that is delivered during a plurality of the charge cycles.

The charge current associated with the voltage stored in the capacitors 208 in any given charge cycle is regulated as a function of the modulation of the timing of each successive conducting state and non-conducting state (duty cycle) for each charge cycle and the frequency of the charge cycles. It should be understood that the modulation of the duty cycle and frequency of the charge cycles is based on actuation of the switch 204. The modulation in turn regulates the charge current that is subsequently generated to replenish the energy that is delivered to capacitors 208.

An average charge current can be defined for each stimulation pulse waveform to be delivered in accordance with treatment regimens of the SIMD 14. The average charge current can be regulated by modulating the frequency of charge cycles and the duty cycle of the charge cycles. In other words, the electrical parameter measured by monitoring devices 210, 212 will be evaluated to determine whether it falls within a predefined range. If the electrical parameter falls outside of the predefined range, the frequency of charge cycles and timing of the durations for each successive conducting and non-conducting states are adjusted to obtain the desired average charge current.

As can be appreciated, the storage capacity of capacitors 208 need only be sufficient to store the voltage that is discharged during a given charge cycle. This is in contrast to the storage capacity that is generally provided in the delivery capacitors of conventional operational circuitry where the energy for delivery of an entire stimulation pulse is stored. The capacitors 208 are configured to hold a voltage based on the charge current delivered by charging circuit 64 and to thereby smooth the waveform of the energy that is delivered to the output circuit 72, such as by removing high-frequency components that may be introduced by the switch 204.

The control circuit 60 will issue the modulation signals that control the opening and closing of the switch 204, as will be described in more detail below. This modulation can be characterized in terms of the on-time and off-time of the switch 204, the duty cycle of each charge cycle, the frequency of the charge cycles and/or the average current delivered for a stimulation pulse.

As described above, the energy generated by charging circuit 64 is delivered through the output circuit 72 to the patient 12 who is connectable through nodes HV-A and HV-B. This generated energy is regulated to create a desired stimulation pulse waveform in accordance with the selected treatment regimen, which is delivered by charging circuit 64. For example, one of the selected treatment regimens may be the aforementioned threshold testing, in which case the waveform may conform to a 50 Hz induction stimulation pulse waveform.

In accordance with embodiments of the present disclosure, a monitoring device 210a or 210b (collectively, "210") may be coupled along the charging path of the stimulation pulse as shown in FIG. 5. The monitoring device 210 is also coupled to the control circuit 60.

As used in this disclosure, the charging path includes an input path, a delivery path and a return path. The input path may be defined as the current path between the power input 202 and the primary side of the voltage converter 200. The delivery path may be defined as the current path between the output of the charging circuit 64 at the secondary side (or secondary sides) of the voltage converter 200, to the output circuit 72, through to the patient 12. The return path may be defined as the current path back from the patient into the output circuit 72, and to the secondary side (or secondary sides) of the voltage converter 200.

In the exemplary embodiment of FIG. 5, the monitoring device 210 may be a resistor that is operable to measure the current flowing through the charging path (e.g., 210a along the return path or 210b along the input path). Although the monitoring devices 210 are illustrated as discrete components, it is contemplated that the functionality of monitoring devices 210 may be integrated into one or more of the components in the charging circuit 64.

In accordance with alternative embodiments, a monitoring device 212a or 212b (collectively, "212") may be coupled to the charging path of the stimulation pulse as shown in FIG. 6. The monitoring device 212 is also coupled to the control circuit 60. In the exemplary embodiment, the monitoring devices 212 may be configured to measure the voltage across an impedance load having a known value during the delivery of the energy to the patient 12.

For example, the voltage across electrodes coupled to nodes HV-A and HV-B may be measured by monitoring device 212a. In this example, the voltage measurement would be across the tissue impedance between HV-A and HV-B, which impedance will have a known measured value. A value of the current flowing through the impedance load may then be calculated based on the measured voltage. That computed current value is utilized by the control circuit 60 to modulate the charging circuit 64 to thereby regulate the charge current being delivered during the induction stimulation pulse. In another example, monitoring device 212b will measure the voltage across the switch 204, which may be embodied as a FET. In that example, the impedance of switch 204 may be predetermined and the voltage across it may be computed as a function of the current flowing through the switch 204. Although the monitoring devices 212 are illustrated as discrete components, it is contemplated that the monitoring devices 212 may be integrated into one or more of the components in the charging circuit 64.

Monitoring devices 210b and 212b are shown in phantom lines to depict alternative placements of the monitoring devices 210a and 212a, respectively. The monitoring devices 210b and 212b will perform a function that is similar to that of monitoring devices 210a and 212a, respectively. Therefore, only one of either monitoring devices 210a and 210*b* (or monitoring devices 212*a* and 212*b* in the alternative embodiment) is needed in any given implementation.

Moreover, the location of the monitoring devices 210, 212 relative to the charging path (e.g., location of monitoring devices 210*a*, 212*a* relative to the return path; or location of monitoring devices 210*b*, 212*b* relative to the input path) is inconsequential—rather, the monitoring device 210, 212 need only be positioned to provide the monitoring and measurement functionality described herein.

In use, the monitoring devices 210*a* and 212*a* are configured to monitor the return path so as to measure an electrical parameter during the delivery of the stimulation pulse. The monitoring devices 210*b*, 212*b* are configured to monitor the input path so as to measure an electrical parameter associated with the power supply to the voltage converter 200.

As shown in FIGS. 5 and 6, the monitoring devices 210, 212 are coupled to the control circuit 60 for transmission of an electrical signal that is representative of the measured electrical parameter to the control circuit 60. The control circuit 60 generates the modulation signal as a function of the electrical signal that is representative of the measured electrical parameter. The modulation signals are issued to the switch 204 to control the actuation of the switch 204 and the actuation of the switch 204 will control the operation of the charging circuit 64 in generating the charge current for the stimulation pulse. In particular, the modulation signals will bias the switch 204 in a conducting or non-conducting state in a manner that will regulate the charge current generated by the charging circuit 64 in accordance with the selected treatment regimen.

For example, the selected treatment regimen may be a threshold test that requires delivery of an induction stimulation pulse waveform having a frequency in the range of 20 to 80 Hz, preferably 50 Hz. As such, the modulation signal generated by the control circuit 60 will control the timing for biasing switch 204 in either the conducting state or the non-conducting state to achieve the appropriate frequency and duty cycle for the charge cycles. The frequency and duty cycle of the generated charge current will define the amplitude of the stimulation pulse waveform that is delivered by output circuit 72. Therefore, the control circuit 60 will modify the modulation signal to adjust the relative timing of the actuation of switch 204 if the electrical parameter that is measured by the monitoring devices 210, 212 indicates that the delivered stimulation pulse waveform associated with a given charge cycle exceeds the predetermined parameters, e.g., the amplitude. This modified modulation signal in turn regulates the charge current for a subsequent charge cycle that is generated by the charging circuit 64. The reverse is also true; the control circuit 60 may issue a modulation signal to modify the generated charge current if the measured electrical parameter is less than a threshold value. While the modulation has been described with respect to a current, the modulation can also be characterized in terms of voltage, instantaneous power, or total energy as a function of the timing of the opening and closing of switch 204.

FIG. 7A depicts an exemplary graph of a voltage waveform 250 and FIG. 7B depicts an exemplary graph of a stimulation pulse waveform 260. The generation of the voltage waveform 250 and the resulting stimulation waveform 260 will be discussed in relation to the operational circuitry described herein.

The waveform 250 represents the voltage delivered to capacitors 208 by the voltage converter 200, while the waveform 260 represents the absolute value of the corresponding energy (current or voltage) that is delivered by the capacitors 208 for generating a stimulation waveform that is delivered by output circuit 72. The waveform 250 is plotted on a two-dimensional graph where the y-axis represents a voltage 252 to which the capacitors 208 are charged and the x-axis represents the time duration for charging the capacitors 208 to the corresponding voltage. The waveform 260 is plotted on a two-dimensional graph where the y-axis represents the absolute value of the amplitude 266 of the energy that is discharged by the capacitors 208 and the x-axis represents the time duration of the discharge of the energy.

The waveform 250 depicts the charge voltage 252 that is stored in capacitors 208 during a plurality of charge cycles 254*a*, 254*b*, 254*c*, 254*d*, . . . , 254*n* and the waveform 260 depicts the absolute amplitude of the stimulation pulses that may be delivered by the output circuit 72. Each charge cycle 254 (e.g., 254*a*) is a function of each adjacent pair of conducting state and non-conducting state of the switch 204. In particular, charge is generated by the voltage converter 200 during each conducting state of switch 204 and discharged during the successive non-conducting state of switch 204 to generate charge voltage that is delivered to the capacitors 208.

The average voltage 256 stored within the capacitors 208 determines the average charge current that is delivered to the output circuit 72 for generating the stimulation pulse waveform 260. The energy generated during each charge cycle (e.g., 254*a*) is stored by capacitors 208 and the average voltage 256 can be regulated by modulating the frequency and duty cycle of the charge cycles. As described above, an electrical parameter is measured during the delivery of the stimulation pulses and a modulation signal may be issued based on the measured electrical parameters to control the parameters associated with the timing for actuation of switch 204. Doing so regulates the delivery of charge current in order to achieve the desired average charge current. The timing parameters will include the frequency of the charge cycles and the timing of the durations for each successive conducting and non-conducting states.

The stimulation pulse waveform 260 is shown as a 50 Hz waveform having multiple pulse periods. Phases 262, 264 represent a single pulse period of stimulation waveform 260 and the phases 262, 264 may be generated by the output circuit 72 described, for example, in co-pending U.S. Ser. No. 14/260,309, by Crutchfield et al., entitled, "Therapy Delivery Methods and Circuits for an Implantable Medical Device," which was filed on Apr. 24, 2014, which is incorporated herein by reference in its entirety. In brief, the H-bridge circuit of output circuit 72 may be operated in a first state to generate phase 262 during an on-state, with the phase 264 representing the off-state segment of the pulse period. If a bipolar stimulation waveform is desired, the H-bridge circuit is utilized to provide the switching that inverts the next pulse period between 20 milliseconds (ms) and 40 ms to generate a negative pulse, which then switches back to deliver a positive phase, and so forth. The duty cycle of the pulse period that includes phases 262 and 264 can be controlled by control circuit 60.

The amplitude 266 is regulated as a function of the frequency of the charge cycles 254, i.e., how quickly the charging circuit 64 replenishes the voltage 252 stored by capacitors 208 to provide the desired average charge current.

The amplitude 266 will correspond to the average voltage 254 (or the average charge current that is delivered by the charging circuit 64 during a plurality of charge cycles 254). The charging circuit 64 will be modulated to generate a regulated charge current for a given charge cycle (e.g., 254*b*) based on an electrical parameter that is measured during the delivery of the charge current in a preceding charge cycle (e.g., 254a). In doing so, the average current for the stimulation pulses can be regulated by continuously or intermittently monitoring the charging path to measure the electrical parameter during delivery of a stimulation pulse waveform resulting from charge current delivered by each charge cycle. As such, the average charge current delivered during both a given charge cycle (e.g., 254a) and the subsequent charge cycle (e.g., 254b) can be controlled to fall within a predetermined value.

The feedback technique may be extended to control an average current delivered in more than two cycles, such as (254a, 254b) so as to generate the stimulation pulse waveform 260. For example, the illustrated stimulation pulse waveform 260 is generated by delivery of charge current over a plurality of charge cycles 254a-n, with the average voltage 256 being regulated to provide the predetermined average charge current. In an embodiment, the operation of charging circuit 64 to generate the charge current is controlled over a plurality of charge cycles so that a predetermined average charge current is delivered. The value of predetermined average charge current associated with each charge cycle is correlated to the amplitude 266. Therefore, generation of charge current in a given charge cycle will be based on measured electrical parameters that are associated with the delivery of charge current for a charge cycle preceding the given charge cycle.

In accordance with the techniques described above, the rate at which charge current is generated by the charging circuit 64 for delivery of a stimulation pulse waveform can be adjusted as a function of the electrical parameter measured by the monitoring devices 210, 212. The rate of generation of the charge current is based on the arbitrary input signals that are provided by the power source 58 through the switch 204. The on-off timing of the switch 204 regulates the charge current that is generated by the charging circuit 64 to the capacitors 208. As such, the charging circuit 64 will provide a real-time regulated charge current to the output circuit 72, and the optional capacitors 208 may provide a filtering function to smooth the energy waveform.

Figure 8:
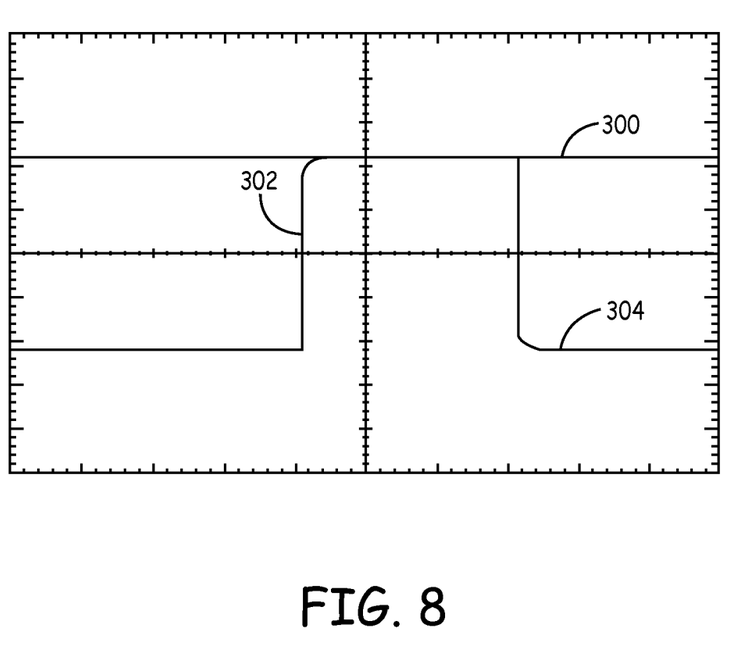
FIG. 8 is a diagram illustrating arbitrary input signals and resulting delivered waveforms delivered by operational circuitry in accordance with embodiments of the disclosure.

FIG. 8 is a diagram illustrating arbitrary input signals (e.g., selected input waveforms) and the resulting waveforms that are delivered using, for example, output circuit 72, such as schematically shown in FIGS. 5 and 6. As used herein, the term "arbitrary" input signal refers to the ability to select any shape of input (e.g., voltage waveform, static DC level input, shaped waveform, etc.) for use in generating a resulting current waveform (e.g., that generally follows the same shape (e.g., a ramped voltage input waveform being used to generate a ramped delivered current waveform, a static input used to deliver a proportional current, etc.)).

A static input signal (e.g., a 1.5 V static input) delivered by capacitors 208 may be utilized to generate a proportional delivered waveform (e.g., measured across a 500 ohm load). For example, when the output circuit 72 is operational and a static input waveform 300 is applied, with the switches 80 and 86 being selected, a stimulus pulse or delivered waveform 302 having a first polarity (e.g., a positive polarity) is applied to the patient 12. Further, for example, when the output circuit 72 is operational with the static input waveform 300 being applied, and the switches 82 and 84 are selected, a stimulus pulse or delivered waveform 304 having a second polarity (e.g., a negative polarity) is applied to the patient 12.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable cardiac stimulation device, comprising:
   at least two electrodes;
   a charging circuit operable to generate a charge current;
   an output circuit coupled to the charging circuit and operable to receive the charge current and to deliver, in response to receiving the charge current, a stimulation pulse through the at least two electrodes in accordance with a treatment regimen;
   a monitoring device coupled to the output circuit, wherein the monitoring device is operable to measure an electrical parameter of the stimulation pulse during delivery of the stimulation pulse; and
   a control circuit coupled to the monitoring device and the charging circuit, wherein the control circuit is configured to issue a modulation signal operable to regulate the generation of the charge current by the charging circuit in response to the measured electrical parameter of the stimulation pulse,
   wherein the charge current for the stimulation pulse comprises a plurality of charge cycles and the modulation signal is configured to control the charging circuit to modify at least one parameter of the charge cycles.

2. The implantable cardiac stimulation device of claim 1, wherein the charging circuit includes:
   a voltage converter operable to generate the charge current, and
   a charge modulation device operable to receive the modulation signal, wherein the charge modulation device is modulated based on the modulation signal to control the voltage converter in generating the charge current.

3. The implantable cardiac stimulation device of claim 2, wherein the charge modulation device controls a timing of the charge current generated by the charging circuit during two or more charge cycles.

4. The implantable cardiac stimulation device of claim 2, wherein the charge modulation device comprises a switch.

5. The implantable cardiac stimulation device of claim 1, wherein the output circuit includes a H-bridge having a high side coupled to a first terminal of the charging circuit and a low side coupled to a second terminal of the charging circuit.

6. The implantable cardiac stimulation device of claim 5, wherein:
   the H-bridge includes a high node, a first node, a second node, and a low node, the high side of the H-bridge includes a first switch coupled between the high node and the first node and a second switch coupled between the high node and the second node, the low side of the H-bridge includes a third switch coupled between the first node and the low node and a fourth switch coupled between the second node and the low node, a first electrode of the at least two electrodes is coupled to the first node, and a second electrode of the at least two electrodes is coupled to the second node.

7. The implantable cardiac stimulation device of claim 1, wherein an amplitude of a waveform of the stimulation pulse is regulated as a function of the measured electrical parameter of the stimulation pulse.

8. The implantable cardiac stimulation device of claim 1, wherein the measured electrical parameter of the stimulation pulse is a current flowing through a charging path defined between the charging circuit and the output circuit.

9. The implantable cardiac stimulation device of claim 1, wherein the monitoring device comprises a resistor.

10. The implantable cardiac stimulation device of claim 1, wherein the measured electrical parameter of the stimulation pulse is a voltage across the at least two electrodes.

11. The implantable cardiac stimulation device of claim 1, wherein the monitoring device comprises a voltage measurement device.

12. The implantable cardiac stimulation device of claim 1, wherein the generated stimulation pulse is configured to induce an arrhythmia in a patient.

13. The implantable cardiac stimulation device of claim 1, further comprising a filtering component configured to smooth a waveform of the stimulation pulse generated by the charging circuit.

14. The implantable cardiac stimulation device of claim 1, wherein the at least one parameter of the charge cycles comprises at least one of a duty cycle and a frequency.

15. An implantable cardiac stimulation device, comprising:
at least two electrodes;
a charging circuit operable to generate a charge current;
an output circuit coupled to the charging circuit and operable to:
receive the charge current,
deliver, in response to receiving the charge current, first stimulation pulses configured to induce an arrhythmia in a patient through the at least two electrodes, and
deliver one or more second stimulation pulses configured to terminate the arrhythmia through the at least two electrodes;
a monitoring device coupled to the output circuit, wherein the monitoring device is configured to measure an electrical parameter of the first stimulation pulses during delivery of the first stimulation pulses; and
a control circuit coupled to the monitoring device and the charging circuit, wherein the control circuit is configured to issue a modulation signal operable to regulate the generation of the charge current by the charging circuit during the delivery of the first stimulation pulses in response to the measured electrical parameter of the first stimulation pulses,
wherein the charge current for the stimulation pulse comprises a plurality of charge cycles and the modulation signal is configured to control the charging circuit to modify at least one parameter of the charge cycles.

16. The implantable cardiac stimulation device of claim 15, wherein the at least one parameter of the charge cycles comprises at least one of a duty cycle and a frequency.

* * * * *